United States Patent [19]

Gravener et al.

[11] 4,379,457
[45] Apr. 12, 1983

[54] INDICATOR FOR SURGICAL STAPLER

[75] Inventors: Roy D. Gravener, Bethany; Alfred F. De Carlo, Stamford; Douglas G. Noiles, New Canaan, all of Conn.

[73] Assignee: United States Surgical Corporation, Norwalk, Conn.

[21] Appl. No.: 234,720

[22] Filed: Feb. 17, 1981

[51] Int. Cl.³ .................... A61B 17/04; A61B 17/08
[52] U.S. Cl. ................. 128/334 R; 128/335; 227/DIG. 1; 227/156
[58] Field of Search .............. 128/325, 326, 334 R, 128/335; 227/19, 119, DIG. 1, 156; 29/243.56

[56] References Cited

U.S. PATENT DOCUMENTS

| | | |
|---|---|---|
| 2,891,250 | 6/1959 | Hirata . |
| 2,940,451 | 6/1960 | Vogelfanger et al. ............. 128/334 |
| 2,965,900 | 12/1960 | Inokouchi . |
| 3,080,564 | 3/1963 | Strekopytov et al. . |
| 3,082,426 | 3/1963 | Miles . |
| 3,144,654 | 8/1964 | Mallina et al. . |
| 3,176,896 | 4/1965 | Mallina ............................ 227/19 |
| 3,191,842 | 6/1965 | Fischer et al. ..................... 227/155 |
| 3,193,165 | 7/1965 | Akhalaya et al. ..................... 227/8 |
| 3,225,996 | 12/1965 | Mallina ............................ 227/137 |
| 3,252,643 | 5/1966 | Strekopytov et al. ............. 227/109 |
| 3,269,630 | 8/1966 | Fleischer ............................ 227/107 |
| 3,269,631 | 8/1966 | Takaro ............................ 227/144 |
| 3,388,847 | 6/1968 | Kasulin et al. ..................... 227/19 |
| 3,494,533 | 2/1970 | Green et al. ..................... 227/19 |
| 3,518,993 | 7/1970 | Blake ............................ 128/321 |
| 3,552,626 | 1/1971 | Astafiev et al. ..................... 227/76 |
| 3,589,589 | 6/1971 | Akopov ............................ 227/153 |
| 3,593,903 | 7/1971 | Astafiev et al. ..................... 227/76 |
| 3,638,652 | 2/1972 | Kelley ............................ 128/305 |
| 3,687,138 | 8/1972 | Jarvik ............................ 128/326 |
| 3,692,224 | 9/1972 | Astafiev et al. ..................... 227/19 |
| 3,790,057 | 2/1974 | Razgulov et al. ..................... 227/19 |
| 3,795,034 | 3/1974 | Strekopytov et al. ............. 29/212 D |
| 3,836,061 | 9/1974 | Grunwald ............................ 227/155 |
| 3,935,981 | 2/1976 | Akopov et al. ..................... 227/19 |
| 4,166,466 | 9/1979 | Jarvik ............................ 128/325 |
| 4,207,898 | 6/1980 | Becht ............................ 128/305 |

FOREIGN PATENT DOCUMENTS 1057729 5/1959 Fed. Rep. of Germany .
587678 1/1959 Italy .
1241577 8/1971 United Kingdom .

OTHER PUBLICATIONS

Japanese Brochure of C. Itoh & Co., Ltd., (prior to Feb. 8, 1979).
"Information Booklet for Auto Suture ® Model EEA Surgical Stapling Instrument and Disposable Fastening Units", (1/79).

Primary Examiner—Michael H. Thaler
Assistant Examiner—C. W. Shedd
Attorney, Agent, or Firm—Robert R. Jackson; John E. Nathan

[57] ABSTRACT

An indicator for a surgical stapler viewable through a window adjacent the handle when the stapler magazine is within a spaced relation range to the stapler anvil; whereby, the staples are properly deformed and the stapled tissue is not inordinately crushed.

13 Claims, 11 Drawing Figures

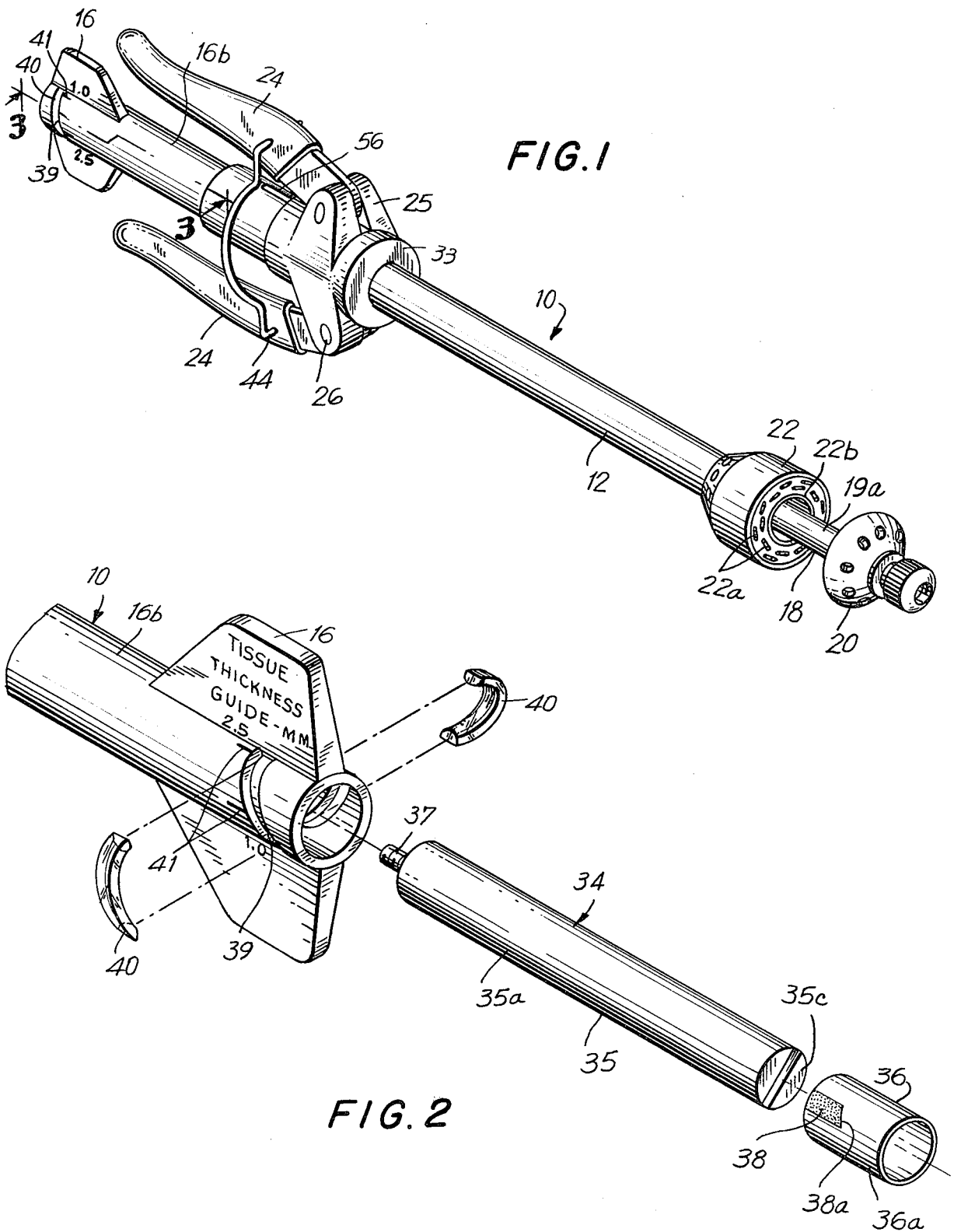

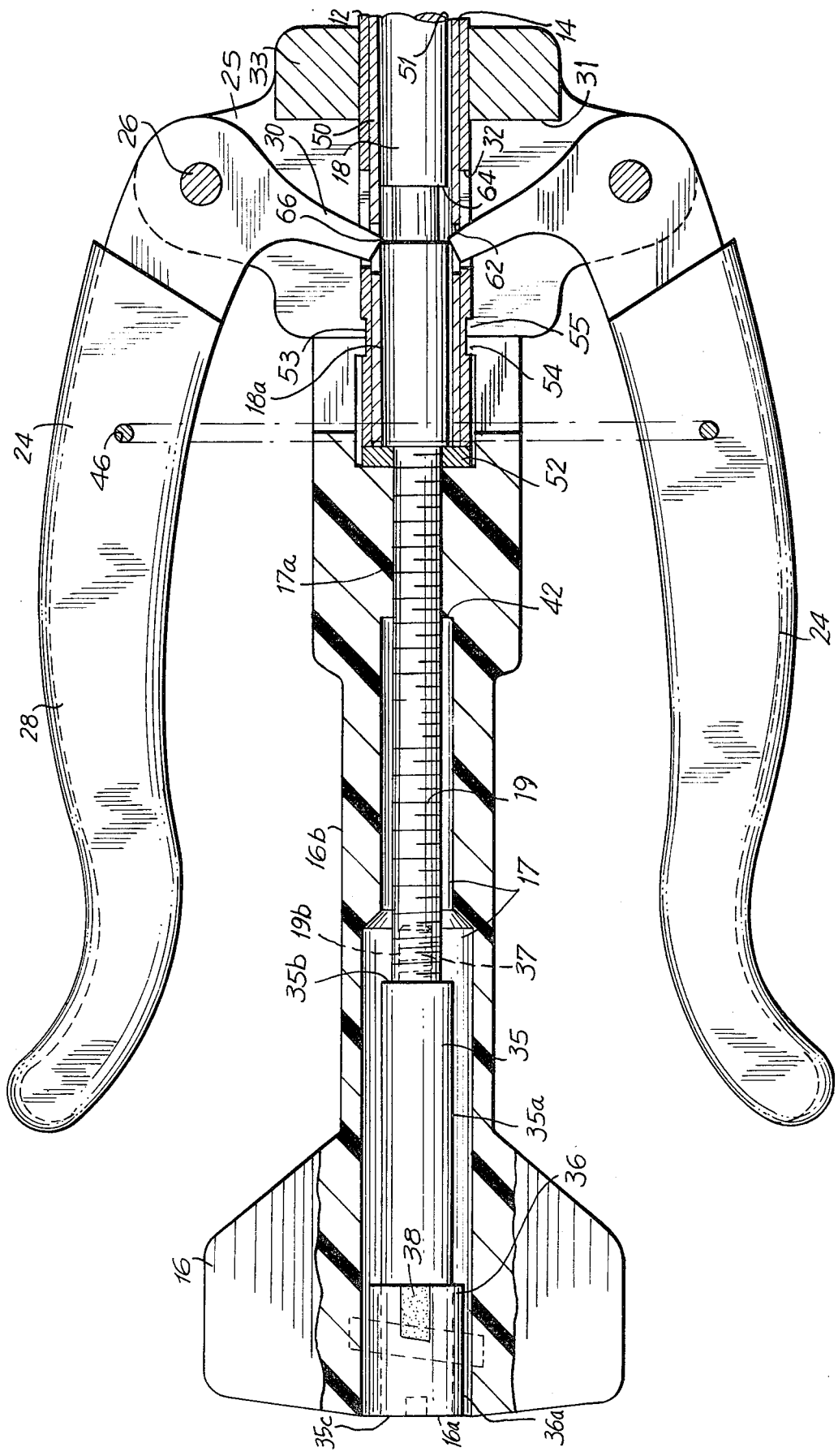

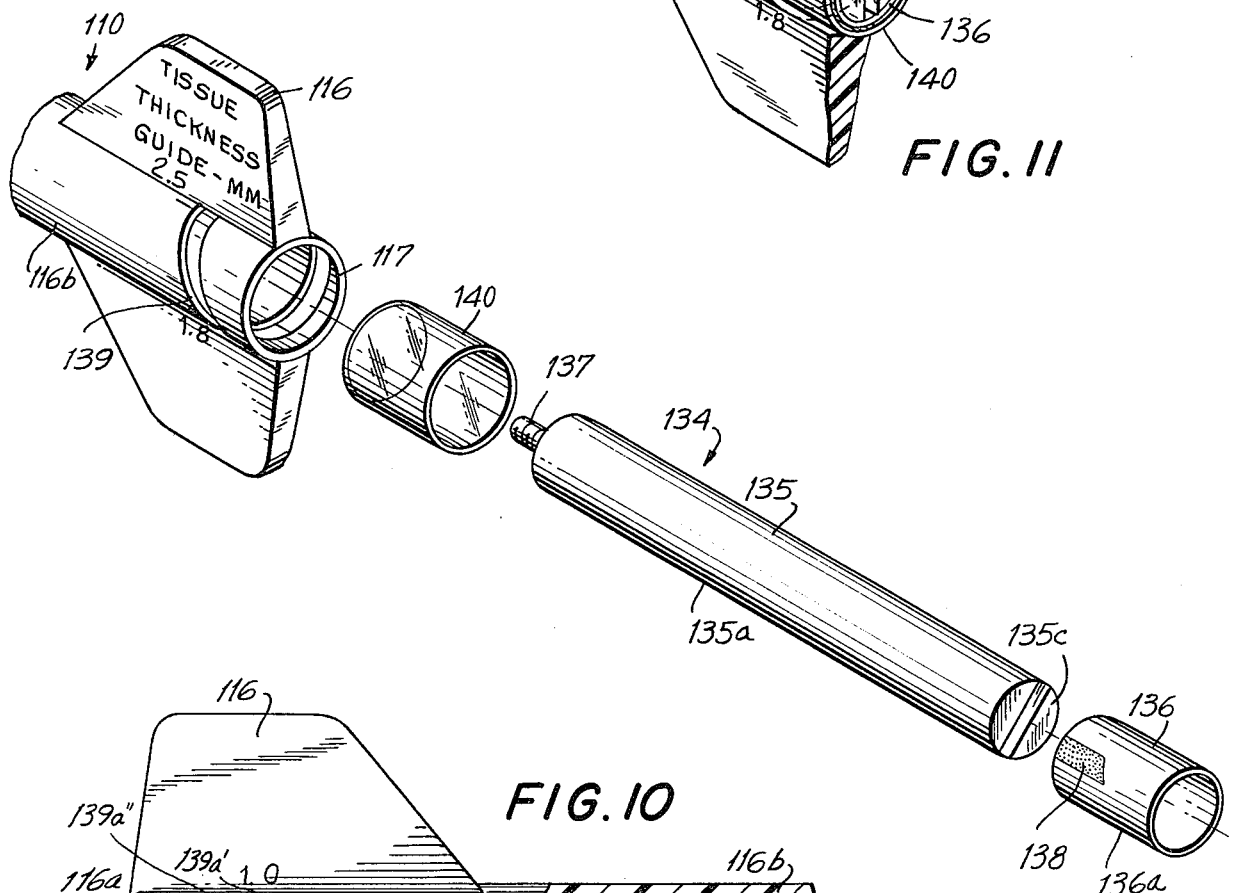

INDICATOR FOR SURGICAL STAPLER

BACKGROUND OF THE INVENTION

This invention relates to a relatively simple and inexpensive instrument for surgical stapling.

A variety of surgical staplers are known in which stapling is carried out at one end of the staplers in the space between their staple carrying parts and their anvils. See, for example, U.S. patent application, Ser. No. 967,421, filed Dec. 7, 1978, entitled "Instrument For Circuler Surgical Stapling Of Hollow Body Organs And Disposable Cartridge Therefor" (a division of which application issued as U.S. Pat. No. 4,304,236), in which a stapler has been described which can have a disposable cartridge assembly, containing surgical staples and a knife, and a cooperating anvil assembly mounted on its distal end before use and removed from it after use. In a stapler of this type, a knob or a wing nut has commonly been provided at the opposite end of the stapler. The knob or wing nut has been adapted to be turned to very significantly the space, between the staple carrying part and the anvil, in which a surgeon manipulates and positions body tissue to be stapled.

Typically, the maximum space between the staple carrying part and the anvil in such a stapler has been from approximately one-half inch to two inches. However, before tissue could be stapled with such a stapler, the space between its staple carrying part and its anvil has had to be reduced to a space that is compatible with the size of the staple being used. For example, when stapling with the common B-shape surgical staple, the space between the staple carrying part and the anvil has had to be reduced to between about 1 mm and 2.5 mm, so that tissue, compressed between the staple carrying part and the anvil, could be suitably fastened together with the stapler.

In order to provide a space between such a stapler's staple carrying part and its anvil that is compatible with the staple being used, so that suitable fastening of tissue can occur, means have been sought for assuring that the space between the staple carrying part and the anvil is suitable for fastening tissue. In pending U.S. patent application, Ser. No. 197,614, filed Oct. 16, 1980, entitled "Disposable Instrument For Surgical Fastening" (now U.S. Pat. No. 4,351,466), a stapler has been described that is provided with an indicator to show when the spacing between its staple carrying part and its anvil is within a range of spacings that is generally suitable for fastening tissue between the staple carrying part and the anvil (This range is hereinafter generally referred to as the "range of generally suitable spacings"). The indicator of that stapler has comprised the proximal end of a movable central rod, carrying the anvil, and the proximal end of a wing nut, threadedly engaged with the central rod. When the wing nut has been turned to move the central rod to a position in which the spacing between the anvil and the staple carrying part is within the range of generally suitable spacings (e.g., within the range of about 1 to 2.5 mm), the proximal end of the central rod has been either flush with, or has extended proximally of, the end of the wing nut.

However, with the stapler of application Ser. No. 197,614, it has not always been possible for a user of the stapler to quickly and accurately tell whether the spacing between its anvil and its staple carrying part has been within the range of generally suitable spacings. In this regard, when the spacing between the anvil and the staple carrying part has been close to the maximum spacing within the range of generally suitable spacings, it has been difficult or impossible to determine visually whether:

(a) the proximal end of the central rod is flush with or extends proximally of the end of the wing nut (i.e., the spacing between the anvil and staple carrying part is within the range of generally suitable spacings); or (b) the proximal end of the central rod is located distally of the end of the wing nut (i.e., the spacing between the anvil and staple carrying part is not within the range of generally suitable spacings).

Thus, means have been sought for telling at a glance whether the spacing between an anvil and a staple carrying part in a surgical stapler is within the range of generally suitable spacings.

SUMMARY OF THE INVENTION

In a surgical stapler, provided with:
 (a) an anvil;
 (b) a staple carrying assembly, located proximally of the anvil; the staple carrying assembly being adapted to be activated, so that its staples are urged distally against the anvil to staple tissue between the anvil and the staple carrying assembly;
 (c) a threaded rod, adapted to move axially and connected to the anvil or to the staple carrying assembly;
 (d) rotatable moving means, located proximally of the staple carrying assembly and threadedly engaged with the threaded rod, for moving the threaded rod axially upon rotation of the moving means; the moving means being rotatably connected to the anvil, if the threaded rod is connected to the staple carrying assembly, or to the staple carrying assembly, if the threaded rod is connected to the anvil; and the portions of the threaded rod, threadedly engaged with the moving means, being located within the moving means; and
 (e) means, connected to the threaded rod and the moving means, for indicating that the axial position of the threaded rod relative to the moving means is such that the spacing between the anvil and the staple carrying assembly is within a range of spacings that is generally suitable for stapling tissue between the anvil and the staple carrying assembly;
an improved indicating means (e) is provided by this invention which comprises:

an indicator marking which is connected to the threaded rod and is adapted to move axially within the moving means between the threaded rod and the moving means; and a helical surface in the lateral surface of the moving means which faces proximally and which substantially parallels the helical path of the indicator marking, relative to the moving means, when the moving means is rotated and the indicator marking is located axially of the helical surface;

the indicator marking not being laterally covered by the moving means and being continuously visible proximally of, and adjacent to, the helical surface as the moving means is rotated when and only when the spacing between the anvil and the staple carrying assembly is within the range of generally suitable spacings.

With this improved indicator for a surgical stapler, it can be determined at a glance whether the spacing between its anvil and staple carrying assembly is within the range of generally suitable spacings.

BRIEF DESCRIPTION OF THE DRAWINGS

FIG. 1 is a perspective view of a surgical stapler, as disclosed in pending U.S. patent application Ser. No. 197,614, provided with one embodiment of the indicator of this invention. FIG. 1 shows the stapler's axially movable, central rod extending as far distally as it will go. In FIG. 1, the anvil assembly, mounted on the distal end of the central rod, is spaced from the staple carrying assembly on the distal end of the stapler's housing.

FIG. 2 is an exploded perspective view of the proximal end of the stapler of FIG. 1. FIG. 2 is a view from the opposite side of the stapler from FIG. 1. FIG. 2 shows the elements of the indicator of this invention, which is connected to the central rod and from which one can quickly and accurately determine whether the spacing between the anvil and staple carrying assemblies is within the range of generally suitable spacings.

FIG. 4 shows the distal surfaces of the pair of windows on opposite sides of the lateral surface of the wing nut on the stapler. The proximal end of the indicator, connected to the central rod, is located distally of the pair of windows, and the pair of indicator markings on opposite sides of the indicator are laterally covered by the wing nut.

FIG. 6 is a fragmentary, partial sectional view, taken along line 6—6 in FIG. 5. FIG. 6 shows the positions of the housing, central rod, pusher, wing nut and indicator of the stapler of FIG. 5 when its handles are ready to be urged towards the housing to urge the pusher distally, so as to activate the staple carrying assembly to fasten tissue together between the anvil and staple carrying assemblies.

FIG. 7 shows the distal surface of each window, and one of the indicator markings on the indicator is visible adjacent to, and proximal of, the distal surface of one of the windows.

FIG. 9 is an exploded perspective view, similar to FIG. 2, of the proximal end of a surgical stapler, provided with an alternative embodiment of the indicator of this invention.

FIG. 10 is a fragmentary, partial sectional view, similar to FIG. 3, of the stapler and the alternative embodiment of the indicator of FIG. 9.

FIG. 11 is a fragmentary perspective view, similar to FIG. 7, showing the proximal end of the stapler of FIG. 9. The proximal end of the indicator is located proximally of a window in the lateral surface of the wing nut of the stapler, and an indicator marking on the indicator is visible adjacent to, and proximal of, the distal surface of the window.

DETAILED DESCRIPTION OF THE PREFERRED EMBODIMENT

Figure 3:
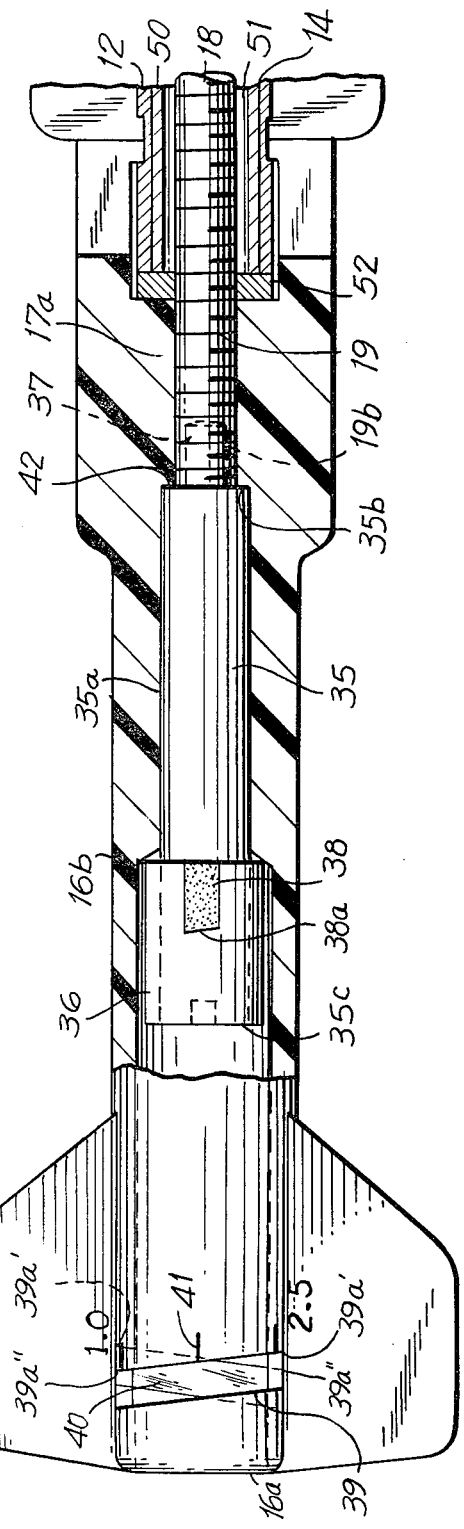
FIG. 3 is a fragmentary, partial sectional view, taken along line 3—3 in FIG. 1.

Although the principles of this invention are applicable to other surgical staplers, the invention will be fully understood from the following explanation of its application to the disposable surgical stapler of pending U.S. patent application Ser. No. 197,614, filed Oct. 16, 1980, entitled "Disposable Instruments For Surgical Fastening", which application is incorporated herein by reference.

Shown in FIGS. 1 to 8 is one embodiment, generally 10, of a surgical stapler, provided with an indicator of this invention. In accordance with application Ser. No. 197,614, the stapler 10 includes an elongated hollow tubular body or housing 12 having an axial bore 14 therethrough. Proximally of the housing 12 is a wing nut 16 having an axial bore 17 therethrough, coaxial with the bore 14 of the housing 12.

Projecting from the distal end of the housing 12 is a central rod 18. The central rod 18 is axially located within the bore 14 of the housing 12 and is adapted to move distally and proximally within the bore 14. The central rod 18 extends distally of, and terminates at a substantial distance from, the distal end of the housing 12. The central rod 18 also extends proximally of the housing 12. The central rod 18 extends into, and is axially located within, the bore 17 of the wing nut 16. The central rod 18 is adapted to move axially within the bore 17.

On the distal end of the central rod 18 is an anvil assembly, generally 20. On the distal end of the housing 12, proximally of the anvil assembly 20, is a staple carrying assembly, generally 22. The anvil assembly 20 and/or the staple carrying assembly 22 can be integral with the stapler 10 or they can be separate pieces that are adapted to be securely attached to the stapler 10 in a predetermined indexed orientation by the user of the stapler in a manner known to those skilled in the art.

The structure and dimensions of the anvil and staple carrying assemblies 20 and 22 are not part of the invention, and any conventional compatible anvil and staple carrying assemblies, such as the anvil and staple carrying assemblies described in U.S. patent application Ser. No. 967,421, filed Dec. 7, 1978, entitled "Instrument For Circular Surgical Stapling Of Hollow Body Organs And Disposable Cartridge Therefor", can be suitably utilized. Preferably, the anvil assembly 20 has two concentric annular rows of staple crimping pockets (not shown) and an annular knife cutting ring (not shown). The staple carrying assembly 22 contains a plurality of surgical staples (not shown) pointing toward the anvil assembly 20 and arranged in two concentric annular rows 22a. Preferably, the staple carrying assembly 22 also contains an annular knife 22b, concentric with, but inside of, the annular staple array. In the stapler 10, activation of the staple carrying assembly 22 causes its knife 22b to be urged distally into the knife cutting ring of the anvil assembly 20 and causes its rows of staples 22a to be urged distally against, and to be crimped by, the pockets of the anvil assembly.

Projecting laterally from opposite sides of the housing 12 of the stapler 10 are a pair of one-piece handles 24. Each handle 24 is pivotally mounted on the tubular wall of the housing 12 by means of an annular yoke 25 about the lateral surface of the tubular wall of the housing 12. The yoke 25 carries a pair of pivot pins 26, laterally spaced from the tubular wall of the housing 12. Each handle 24 comprises a first handle part 28, located on the side of its pivot pin 26 remote from the housing 12, and a second handle part 30, located on the other side of its pivot pin 26. Each second handle part 30 extends into an axial slot 31 in the yoke 25 and an axial slot 32 in the housing 12. As seen from FIG. 6, the slots 31 extend medially through opposite sides of the yoke 25 and extend distally from the proximal end of the yoke to an annular ring 33 adjacent the distal end of the yoke 25. The slots 31 in the yoke 25 permit the second handle parts 30 to move medially and distally into the slots 32 in opposite sides of the housing 12. As also seen from FIG. 6, the slots 32 in the housing 12 extend medially through its tubular wall and proximally of the pivot pins 26.

The dimensions and locations of the slots 31 and 32 are such in the stapler 10 that the second handle parts 30 can move distally and medially a substantial distance through the slots 31 and 32 upon movement of the first handle parts 28 towards the wing nut 16 and the housing 12 (within the wing nut 16) without interference from the yoke 25 or the tubular wall of the housing 12. In this regard, each slot 31 and 32 is somewhat wider than each second handle part 30 and extends proximally from about the pivot pins 26. Preferably, the proximal end of each slot 32 in the housing 12 extends far enough distally to prevent each second handle part 30 from moving laterally outward of the slot 32 when the first handle parts 28 are moved laterally away from the housing 12 and wing nut 16.

Rotation of the wing nut 16 of the stapler 10 can be used to move the central rod 18 either distally or proximally within the axial bore 14 of the housing 12 and within the axial bore 17 of the wing nut 16. This is because a reduced diameter portion 19 of the central rod 18, adjacent its proximal end, is provided with threads which mate with threads on a constricted portion 17a of the axial bore 17 of the wing nut 16 as shown in FIGS. 3 and 6.

Another portion 19a of the central rod 18, adjacent its distal end, has a pair of axial keyways (not shown) on opposite sides of the central rod. A pair of keys (not shown) is provided on opposite sides of the interior surface of the staple carrying assembly 22 adjacent the central rod 18, and a second pair of keys (not shown) is provided on opposite sides of the interior surface of the anvil assembly 20 adjacent the central rod 18. The keys fit into the keyways to prevent rotation of the central rod 18 relative to the housing 12 when the wing nut 16 is rotated to move the central rod 18 axially and to assure that the anvil and staple carrying assemblies 20 and 22 are in a predetermined indexed orientation on the central rod 18 for proper fastening of tissue.

Provided on the proximal end of the central rod 18 of stapler 10 is an indicator, generally 34, in accordance with this invention. If desired, the indicator 34 can be integral with the central rod 18. However, as best shown in FIG. 2, the indicator 34 preferably comprises a generally cylindrical, indicator screw 35, attached to the central rod 18. The indicator 34 also preferably comprises a generally tubular indicator sleeve 36, frictionally held on the proximal portions of the lateral surface 35a or the indicator screw 35. The indicator 34 and its indicator screw 35 and indicator sleeve 36 are located within the bore 17 of the wing nut 16.

The distal end 35b of the indicator screw 35 is provided with a threaded projection 37. The projection 37 is screwed into a threaded hole 19b in the proximal end of the central rod 18. The combined axial length of the central rod 18 and indicator screw 35 (when screwed together) and the combined axial length of the coaxial bores 14 and 17 through the housing 12 and wing nut 16 are preferably such that, when the proximal end 35c of the indicator screw 35 is flush, i.e., coplanar, with the proximal surface 16a of the wing nut 16, the anvil assembly 20 is spaced from the staple carrying assembly 22 within the range of generally suitable spacings.

The indicator sleeve 36 is provided on its lateral surface 36a, on diametrically opposite sides thereof, with a pair of axially extending indicator markings 38. Each indicator marking 38 is located between the lateral surface of the central rod 18 and the inside surface of the bore 17 of the wing nut 16. Preferably, each indicator marking 38 is adjacent to the distal end of the indicator sleeve 36 and is provided with a readily visible color (e.g., red) which contrasts with the color (e.g., white) of the lateral surface 36a of the indicator sleeve.

Also in accordance with this invention, a pair of windows 39 are provided on diametrically opposite sides of the lateral surface 16b of the wing nut 16 as best shown in FIGS. 2 and 3. Each window 39 is located in the wing nut 16 where one of the indicator markings 38 of indicator 34, connected to the central rod 18, is located when the spacing between the anvil and staple carrying assemblies 20 and 22 is within the range of generally suitable spacings. The location and shape of the windows 39 are such that each one of the indicator markings 38 is not laterally covered by the lateral surface 16b of the wing nut 16, but rather is continuously visible to a user of the stapler 10 through a different one of the windows 39, proximally of, and adjacent to, the distal surface 39a of a different one of the windows 39, as the wing nut 16 is rotated when and only when the spacing between the anvil the staple carrying assemblies is within the range of generally suitable spacings. In this regard, when the spacing between the anvil and staple carrying assemblies is not within the range of generally suitable spacings, the indicator markings 38 are laterally covered by the lateral surface 16b of the wing nut 16 and hence are not visible through the windows 39.

Figure 7:
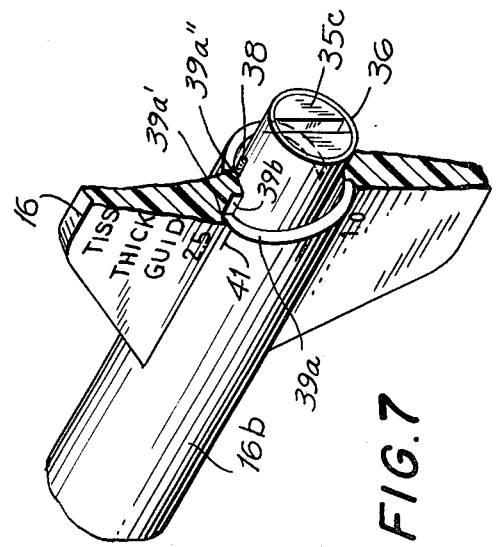
FIG. 7 is a fragmentary perspective view similar to FIG. 4, showing the proximal end of the stapler of FIG. 5 with the proximal end of the indicator being located proximally of the pair of windows.
Figure 4:
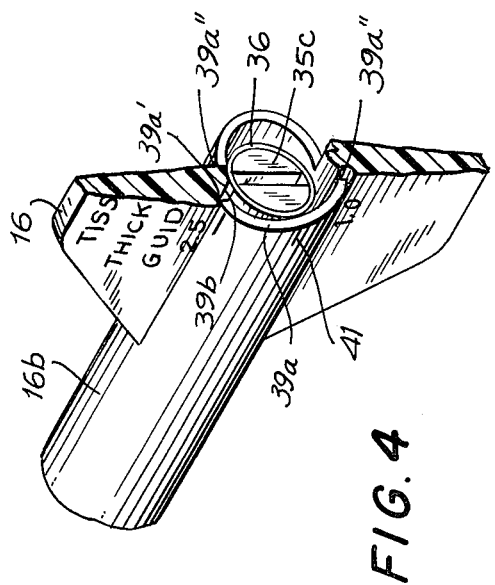
FIG. 4 is a fragmentary perspective view of the proximal end of the stapler of FIG. 1.

As best seen from FIGS. 4 and 7, each window 39, particularly its distal surface 39a, has a helical shape, conforming to the helical path of travel of one of the indicator markings 38, relative to the wing nut 16, as the wing nut 16 is rotated one half turn to move the anvil assembly 20 axially relative to the staple carrying assembly 22 within the range of generally suitable spacings. In this regard, each window 39 and its distal surface 39a define one half turn of a helix which has the same advance per turn as the engaged threads of the wing nut 16 and central rod 18. Hence, the distal surface 39a of each window 39 comprises a helical surface 39a in the lateral surface 16b of the wing nut 16 which helical surface faces proximally and which substantially parallels the helical path of an indicator marking 38, relative to the wing nut, when the wing nut is rotated and the indicator marking is located axially of the helical surface 39a. As also best seen from FIGS. 4 and 7, the distal end 39a' of the distal surface 39a of either window 39 is offset axially from the proximal end 39a" of the distal surface 39a of the other window 39 by half the lead distance of the engaged threads of the wing nut 16 and central rod 18, i.e., by the advance of each indicator marking 38 during one half turn of the wing nut 16. As a result, the axially offset distal and proximal ends 39a' and 39a" of the distal surfaces 39a of the windows 39 form a pair of axially extending shoulders 39b in diametrically opposite sides of the lateral surface 16b of the wing nut 16.

The particular dimensions of each window 39 are not critical. However, the axial width of each window 39 is preferably about twice the axial length of the exposed part of each indicator marking 38, so that all of the portions of the indicator markings 38, proximal of the distal surfaces 39a of the windows 39, are clearly visible through the windows 39 when the spacing between the anvil and staple carrying assemblies 20 and 22 is within the range of generally suitable spacings. Preferably, a clear plastic, magnifying lens 40 is also provided in each window 39 to enhance the visibility of each indicator marking 38 in each window 39.

The axial length of the exposed part of each indicator marking 38 equals the advance of the indicator marking during one half turn of the wing nut 16. Preferably, each indicator marking 38 also has a substantially rectangular shape. In this regard, it is particularly preferred that the proximal end 38a of each indicator marking 38 form an angle with the distal end of the indicator sleeve 36, which angle is approximately the same as the one half turn of a helix defined by the distal surface 39a of each window 39. Thereby, no portion of the indicator markings 38 will be visible through the windows 39 of the wing nut 16 until the spacing between the anvil and staple carrying assemblies 20 and 22 is within the range of generally suitable spacings.

If desired, two sets of parallel, axially extending, indicia 41 can be provided about the circumference of the lateral surface 16b of the wing nut 16 as best shown in FIGS. 2 and 3. The sets of indicia 41 are on opposite sides of the wing nut 16. Each set of indicia 41 is adjacent to a different one of the windows 39, and each indicia in each set is located axially of its adjacent window 39. Each indicia 41 is associated with a specific spacing between the anvil assembly 20 and the staple carrying assembly 22 (within the range of generally suitable spacings) when an indicator marking 38 is visible through a window 39 and is located axially of the indicia 41. The indicia 41 can be calibrated in conventional units of length and can cover a range of spacings equal to the advance of the indicator markings 38 during one half turn of the wing nut 16. The indicia 41 enable the user of stapler 10 to: (a) determine the spacing between the anvil and staple carrying assemblies and (b) provide a selected spacing between the anvil and staple carrying assemblies, e.g., a spacing corresponding to the thickness of the tissue that is to be fastened. In this regard, a selected spacing between the anvil and staple carrying assemblies can be obtained simply by rotating the wing nut 16 until each indicator marking 38 is visible through one of the windows 39 and is located axially of a specific indicia 41 on the wing nut 16 that corresponds to the selected spacing.

The number of indicia 41 and their location are not critical. In this regard, the number of indicia 41 will depend on how precise a spacing is desired between the anvil and staple carrying assemblies 20 and 22. As seen from the embodiment of FIGS. 1 to 8, a set of three indicia 41 can be used for dividing up a range of spacings between anvil and staple carrying assemblies of 1.5 mm (e.g., 2.5 mm to 1.0 mm). However, as shown in the alternative embodiment of FIGS. 9 to 11, the use of a set containing more than three indicia, e.g., six indicia 141, also can be used for dividing up such a range of spacings.

In accordance with this invention, when the spacing between the anvil and staple carrying assemblies 20 and 22 is within the range of generally suitable spacings, each indicator marking 38 is: (a) located opposite, and is visible in, a different one of the windows 39 in the wing nut 16; (b) is visible proximally of, and adjacent to, the distal surface 39a of a different one of the windows 39; and (c) is located axially of an indicia 41 or axially between two indicia 41 on the wing nut 16. This permits a user of the stapler 10 to tell at a glance that the spacing between the anvil and staple carrying assemblies is within the range of generally suitable spacings. This also permits the spacing between the anvil and staple carrying assemblies to be readily varied by simply rotating the wing nut 16 to move the central rod 18, the anvil assembly 20, and the indicator 34 axially until each indicator marking 38 is positioned axially of an indicia 41, associated with a desired spacing between the anvil and staple carrying assemblies.

Also in accordance with this invention, when the spacing between the anvil and staple carrying assemblies is not within the range of generally suitable spacings, neither indicator marking 38 is located opposite, or is visible in, one of the windows 39 in the wing nut 16. Rather, each indicator marking 38 is located distally of the distal surface 39a of each window 39 and hence is covered by the lateral surface 16b of the wing nut 16. It is only when the wing nut 16 is rotated to move the indicator markings 38 proximally from (a) their position, shown in FIG. 4, wherein they are covered by the wing nut towards (b) their position, shown in FIG. 7, wherein they are proximal of the distal surfaces 39a of the windows 39, that they emerge from under the shoulders 39b between the distal ends 39a' and the proximal ends 39a" of the distal helical surfaces 39a of the windows 39 and emerge from under the lateral surface 16b of the wing nut 16. As the wing nut 16 is then rotated further, to move rod 18 and the indicator markings 38 proximally toward their position in FIG. 7, each indicator marking 38 appears to move, relative to the wing nut 16, along a helical path, parallel to the distal helical surface 39a of a different one of the windows 39, for a half turn of the wing nut from: (a) the distal end 39a' of the distal surface 39a, adjacent to the first indicia 41 on one side of the wing nut which represents a maximum suitable spacing (e.g., 2.5 mm) between the anvil and staple carrying assemblies for proper tissue fastening, to (b) the proximal end 39a" of the distal surface 39a, adjacent to the last indicia 41 on the same side of the wing nut 16 which represents a minimum suitable spacing (e.g., 1.0 mm) between the anvil and staple carrying assemblies for proper tissue fastening as shown in FIG. 7. In this regard, as the wing nut 16 is rotated one half turn, each indicator marking 38 is continuously visible as a constant axial length while it appears to travel along the one half turn, helical, distal surface 39a of one of the windows 39. Hence, a user of stapler 10 can tell at a glance, simply by looking at either side of the wing nut 16 to see if one of the indicator markings 38 is visible through one of the windows 39, whether the spacing between the anvil and staple carrying assemblies is within the range of generally suitable spacings. Preferably the proximal translation of central rod 18 is stopped by washer 52 at the same time indicator marking 38 comes into register with the last indicia 41, which condition corresponds to the minimum suitable spacing.

As seen from FIG. 3, the lateral surface 35a of the indicator screw 35 extends laterally of the threaded portion 19 of the central rod 18. As a result, when the central rod 19 is moved to carry the anvil assembly 20 distally, away from the staple carrying assembly 22, to its maximum extent, the distal end 35b of the indicator screw 35 is adapted to abut against an inwardly projecting shoulder 42 that is located in the bore 17 of the wing nut 16, proximally of the threaded constricted portion 17a of the bore 17. The distal end 35b of the indicator screw 35 and the shoulder 42 serve to restrict distal movement of the central rod 18.

As seen from FIG. 6, a tubular pusher 50 is provided within the axial bore 14 of the housing 12 of the stapler 10. The pusher 50 is adapted to move axially within the bore 14. The distal end of the pusher 50 is particularly adapted to move distally within the proximal end of the staple carrying assembly 22 and into the staple carrying assembly to activate the staple carrying assembly, so that its knife 22b is urged distally into the knife cutting ring of the anvil assembly 20 and so that its rows of staples 22a are urged distally against the pockets of the anvil assembly to crimp the staples, so as to cut and fasten tissue. The central rod 18 is located within the axial bore 51 of the pusher 50 and is adapted to move axially within the bore 51. The pusher 50 is located distally of the constricted threaded portion 17a of the axial bore 17 of the wing nut 16. To protect the wing nut 16, about the constricted portion 17a of its axial bore 17, from being harmed by (a) the pusher 50, (b) the housing 12 or (c) the portions of the central rod 18 that are located distally of its restricted diameter portion 18, an annular thrust washer 52 is provided about the restricted diameter portion 18 of the central rod 18, proximally of the pusher 50 and housing 12.

As also seen from FIG. 6, an annular groove 53 is provided in the lateral surface of the housing 12 near its proximal end. Also, an inwardly extending, annular shoulder 54 is provided on the distal end of the axial bore 17 of the wing nut 16, and an inwardly extending, annular shoulder 55 is provided on the proximal end of the yoke 25. The wing nut shoulder 54 and the yoke shoulder 55 engage the groove 53 in the housing 12, so that the distal end of the wing nut 16 abuts the proximal end of the yoke 25.

As also seen from FIG. 6, the pusher 50 has a pair of axial slots 62 on its opposite sides extending through its tubular wall. The width of each slot 62 is somewhat greater than the width of one of the second handle parts 30. The distal end of each slot 62 is located, so that it can be urged distally by a second handle part 30 as the second handle part moves distally and medially when its first handle part 28 is pressed towards the housing 12. The distal ends of the slots 62 also are so located that they can be moved distally a sufficient distance by distal movement of the second handle parts 30, so that the staple carrying assembly 22 is activated by the distal movement of the pusher 50.

As also seen from FIG. 6, a circumferential axial groove 64 is provided in the lateral surface 18a of the central rod 18. The proximal end of the groove 64 is located, so that the end 66 of each second handle part 30, remote from its pivot pin 26, can move medially into the groove 64 without abutting against the lateral surface 18a of the central rod 18, proximally of the groove 64, when the first handle parts 28 are pressed towards the housing 12 and when (as shown in FIG. 6) the indicator markings 38 are visible in the windows 39 in the wing nut 16. Also, the distal end of the groove 64 is located, so that the remote end 66 of each second handle part 30 can move distally in the groove 64 without abutting against the distal end of the groove 64 until the staple carrying assembly 22 is activated by distal movement of the pusher 50.

As further seen from FIG. 6, each second handle part 30 extends through one of the axial slots 31 in yoke 25, one of the axial slots 32 in the housing 12 and into one of the axial slots 62 in the pusher 50. In accordance with this invention, when (as shown in FIG. 3) the indicator markings 38 are not visible in the windows 39 of the wing nut 16, the remote end 66 of each second handle part 30 abuts against the lateral surface 18a of the central rod 18, proximally of its groove 64, and cannot move distally and medially into the groove 64. Only when (as shown in FIG. 6) the indicator markings 38 are visible in the windows 39 of the wing nut 16 is the remote end 66 of each second handle part 30 free to move distally and medially into the groove 64 in the central rod 18 without abutting against the lateral surface 18a of the central rod 18, proximally of its groove 64. This is because the end 66 of each second handle part 30, remote from its pivot pin 26, is spaced from the pivot pin by a distance greater than the lateral distance from the pivot pin to the lateral surface 18a of the central rod 18.

Assembly of the indicator 34 of this invention can be accomplished on the central rod 18 of the stapler 10 by initially rotating the wing nut 16 to move the central rod 18 proximally. The wing nut 16 is rotated until it cannot be rotated any further. At this point, the central rod 18 abuts against the thrust washer 52. The threaded projection 37 on the distal end 35b of the indicator screw 35 is then inserted into, and threadedly engaged with, the threaded hole 19b in the proximal end of the central rod 18. After the indicator screw 35 is attached to the central rod 18 with the threaded projection 37, the proximal end 35c of the indicator screw is approximately flush with the proximal end 16a of the wing nut 16. Then, the indicator sleeve 36 is inserted into the proximal end of the bore 17 of the wing nut 16 and urged to slide distally over the proximal end 35c and the lateral surface 35a of the indicator screw 35. The indicator sleeve 36 is urged distally over the proximal end and lateral surface 35a of the indicator screw 35 in such a manner that each of its indicator markings 38 is located proximally of the proximal end 39a'' of the distal surface 39a of a window 39 and axially of the last indicia 41 (e.g., 1.0 mm) on each side of the wing nut 16. The indicator sleeve 36 is urged distally on the indicator screw 35 until each indicator marking 38: (a) is visible through a window 38, (b) is adjacent to the distal surface 39a of the window 39, and (c) extends proximally from the distal surface 39a by the length of the advance of the indicator marking 38 during one half turn of the wing nut 16, so that the indicator marking 38 will not be visible through a window 39 when the wing nut 16 is turned one half turn, back the other way, to move the central rod 18 and the indicator 34 distally.

Figure 5:
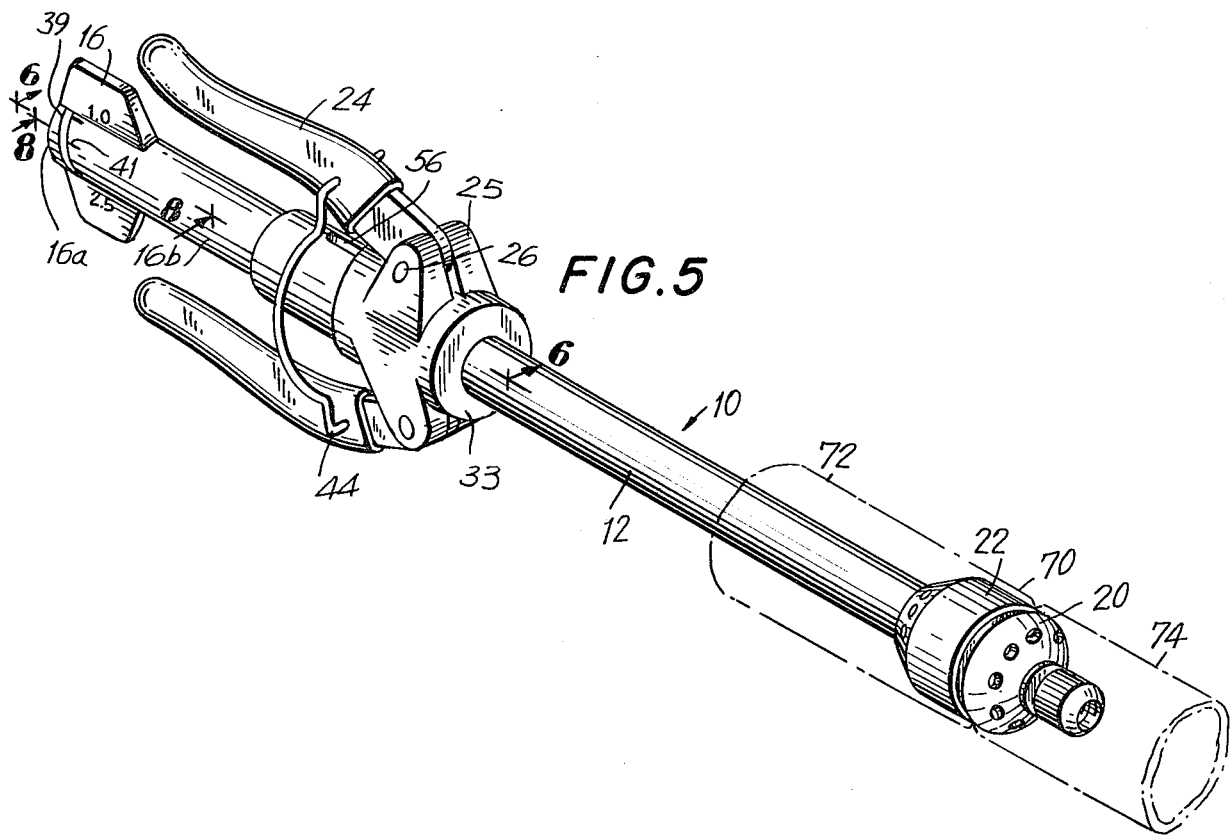
FIG. 5 is a perspective view of the stapler of FIG. 1, showing its anvil assembly and staple carrying assembly clamping sections of a hollow body organ together before the sections are fastened together.
Figure 8:
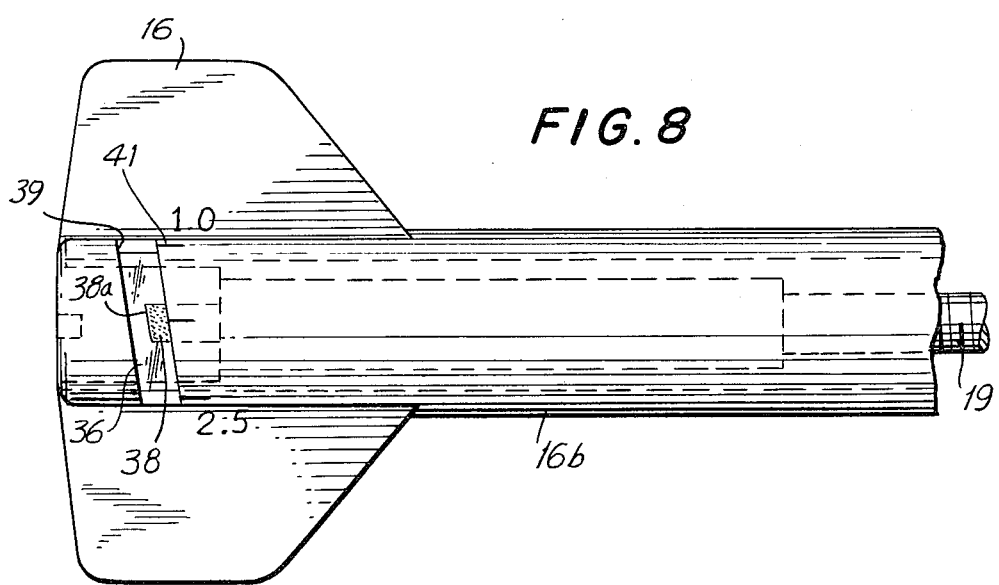
FIG. 8 is a partial plan view of the wing nut of the stapler of FIG. 5, taken along line 8—8 in FIG. 5.

The use of the stapler 10 in an anastomosis procedure is schematically shown in FIGS. 1 and 5. After diseased tissue of a hollow organ 70 has been removed by conventional techniques, the distal end of the stapler is inserted through a first hollow section 72 of the two sections of tissue 72 and 74 to be anastomosed (e.g., the stapler is inserted through the rectum in anastomosis of the large intestine using the rectal approach), so that only the anvil assembly 20 extends beyond the end of the first tissue section 72. The anvil assembly 20 is then moved distally of the staple carrying assembly 22 by rotating the wing nut 16 to the position shown in FIG. 1. Rotating the wing nut 16 causes the central rod 18 to move distally through the bore 51 of the pusher 50 until the distal end 35b of the indicator screw 35 abuts against the annular shoulder 42 within the axial bore 17 of the wing nut 16. The end of the first section of tissue 72 is then fitted over the staple carrying assembly 22 and tied around the central rod 18. The end of the second tissue section 74 is fitted over the anvil assembly 20 and tied around the central rod 18. The well-known "purse string" suture may be used to secure the tissue of the hollow organs around the central rod 18.

The wing nut 16 is then rotated again in the opposite direction to move the central rod 18 and the anvil assembly 20 proximally. The wing nut 16 is rotated until the indicator markings 38 on the indicator sleeve 36 are visible through the windows 39 in the wing nut 16. This means that the spacing of the anvil assembly from the staple carrying assembly is within the range of generally suitable spacings. As a result, tissue can be fastened with the stapler 10 simply by squeezing its handles 24 toward its housing 12.

If desired, a smaller spacing can be provided between the anvil and staple carrying assemblies (e.g., for fastening tissue that is somewhat thinner than normal). This can be done by rotating the wing nut 16 further to move the anvil assembly further proximally until, as viewed through the windows 39, the indicator markings 38 on the opposite sides of the indicator sleeve 36 are positioned axially of indicia 41 on the wing nut 16, which indicia are associated with the desired smaller spacing between the anvil and staple carrying assemblies.

If desired, a larger spacing can also be provided between the anvil and staple carrying assemblies (e.g., for fastening tissue that is somewhat thicker than normal). This can be done by rotating the wing nut 16 to move the anvil assembly distally until, as viewed through the windows 39, each indicator marking 38 on the indicator sleeve 36 is positioned axially of an indicia 41, associated with the desired larger spacing between the anvil and staple carrying assemblies.

When the desired spacing of the anvil and staple carrying assemblies has been achieved, the stapler can be used to fasten the tissue sections 72 and 74. A wire safety lock 44 is removed from the holes 46 in the first handle parts 28. The handles 24 are then squeezed, so that the first handle parts 28 are urged towards the wing nut 16 and husing 12. This causes the second handle parts 30 to rotate about the pivot pins 26 and to move distally and medially through the axial slots 31 in the yoke 25 and through the axial slots 32 in the housing 12. This also causes the second handle parts 30 to move: distally and medially through the axial slots 62 in the pusher 50; distally and medially into the axial groove 64 in the central rod 18; and distally against the distal edges of the slots 62 in the pusher 50. Such movement of the second handle parts 30 is without interference from any portions of the lateral surface 18a of the central rod 18, such as the portions proximal of its groove 64, and such movement can continue until the second handle parts 30 abut against the distal end of the groove 64 in the central rod 18. In this regard, squeezing the handles 24 causes each second handle part 30 to move medially and distally and to urge the distal edge of a slot 62 in the pusher 50 distally, to move the pusher 50 distally until the staple carrying assembly is activated by the pusher 50 and until the staples are urged distally against the pockets of the anvil assembly through the approximated sections of tissue, the staples are crimped by the pockets of the anvil assembly, and the portions of the sections of tissue between their securing sutures and the staples are cut by the annular knife and the knife cutting ring.

Shown in FIGS. 9 to 11 is another embodiment, generally 134, of an indicator of this invention. The indicator 134 is associated with a surgical stapler, generally 110, which is virtually the same as the stapler 10 of FIGS. 1 to 9. In the stapler 110 and indicator 134 of FIGS. 10 to 12, elements corresponding to the elements of the stapler 10 and indicator 34 of FIGS. 1 to 9 have reference numerals which differ by one hundred (100) from the elements of the stapler 10 and the indicator 34 of FIGS. 1 to 9.

In the indicator 134 of FIGS. 9 to 11, an indicator screw 135 is provided having an indicator sleeve 136, frictionally held on the proximal end of its lateral surface 135a. Provided on the distal end 135b of the indicator screw 135 is a threaded projection 137 which can be threaded into a hole in the proximal end of a central rod (not shown) of the stapler 110. Adjacent the distal end of the indicator sleeve 136, on the lateral surface 136a thereof, is a single, axially extending, indicator marking 138.

Provided in the lateral surface 116b of the wing nut 116 of the fastener 110 is a single window 139 which extends on both sides of the wing nut 116. A clear plastic tubular magnifying lens 140 is inserted in the proximal end of the bore 117 of the wing nut 116 and in the window 139.

A single set of parallel, axially extending indicia 141 can, if desired, be provided about the circumference of the lateral surface 116b of the wing nut 116. Each indicia 141 is located axially of, and adjacent to, the window 139. Each indicia 141 is associated with a specific spacing between the anvil and staple carrying assemblies (not shown) of the stapler 110 when the indicator marking 138 is visible through the window 139 and is located axially of the indicia.

The stapler 110 and its indicator 134 are adapted to have the single indicator marking 138 continuously visible through the single window 139 in the wing nut 116 as the wing nut 116 is rotated one full turn when and only when the spacing between the anvil and staple carrying assemblies of the stapler 110 is within the range of generally suitable spacings. In this regard, the indicator marking 138 is laterally covered by the wing nut 16 and is not visible when the spacing between the anvil and staple carrying assemblies is not within the range of generally suitable spacings. The window 139 and its distal surface 139a preferably have a helical shape conforming to the helical path of travel of the indicator marking 138, relative to the wing nut 116, as the wing nut 116 is rotated one full turn.

As the wing nut 116 is rotated to move the central rod and the anvil assembly proximally, so that the anvil and staple carrying assemblies are brough within the range of generally suitable spacings, the indicator marking 138 appears in the window 139 after emerging from under a shoulder 139b of the wing nut 116 between the distal end 139a' and the proximal end 139a" of the distal surface 139 of the window 139. The indicator marking 138 then appears to move, relative to the wing nut 116, along a helical path, parallel to the helical distal surface 139a of the window 139 for one full turn of the wing nut 116 from: (a) the distal end 139a' of the distal surface 139a of the window 139, adjacent to the first indicia 141 on one side of the wing nut 116 which represents a maximum suitable spacing (e.g., 2.5 mm) between the anvil and staple carrying assemblies for proper tissue fastening to (b) the proximal end 139a" of the distal surface 139a of the window 139, adjacent to the last indicia 141 on the other side of the wing nut 116 which represents a minimum suitable spacing (e.g., 1.0 mm) between the anvil and staple carrying assemblies for proper tissue fastening as shown in FIG. 11.

Unlike the indicator markings 38 of the stapler 10 of FIGS. 1 to 8, the indicator marking 138 of the stapler 110 of FIGS. 9 to 11 is visible through the window 139 of the wing nut 116 for almost one full turn of the wing nut 116. Thus, the visible travel of the indicator marking 138 of the stapler 110 is almost twice as far as the visible travel of each of the two indicator markings 38 of the stapler 10 of FIGS. 1 to 8. As a result, the single indicator marking 138 of the stapler 110 can provide a more accurate determination of the spacing between the anvil and staple carrying assemblies of the stapler 110 than can the pair of indicator markings 38 in the stapler 10 of FIGS. 1 to 8. Nevertheless, for telling at a glance that the spacing between anvil and staple carrying assemblies of a stapler, as disclosed, for example, in pending application Ser. No. 197,614, is within the range of generally suitable spacings, the indicator 34 with its pair of indicator markings 38, the pair of windows 39 and the two sets of indicia 41 of the stapler 10 of FIGS. 1 to 8 are generally preferred.

It will be understood that the embodiments shown and described herein are merely illustrative of the principles of the invention and that various modifications can be made by those skilled in the art without departing from the spirit and scope of the invention, the forms hereinbefore described being merely preferred embodiments.

We claim:

1. In a surgical stapler, provided with:
   (a) an anvil;
   (b) a staple carrying assembly, located proximally of the anvil; the staple carrying assembly being adapted to be activated, so that its staples are urged distally against the anvil to staple tissue between the anvil and the staple carrying assembly;
   (c) a threaded rod, adapted to move axially and connected to the anvil or to the staple carrying assembly;
   (d) rotatable moving means, located proximally of the staple carrying assembly and threadedly engaged with the threaded rod, for moving the threaded rod axially upon rotation of the moving means; the moving means being rotatably connected to the anvil, if the threaded rod is connected to the staple carrying assembly, or to the staple carrying assembly, if the threaded rod is connected to the anvil; and the portions of the threaded rod, threadedly engaged with the moving means, being located within the moving means; and
   (e) means, connected to the threaded rod and the moving means, for indicating that the axial position of the threaded rod relative to the moving means is such that the spacing between the anvil and the staple carrying assembly is within a range of spacings that is generally suitable for stapling tissue between the anvil and the staple carrying assembly;
the improved indicating means (e) which comprises:
   an indicator marking which is connected to the threaded rod and is adapted to move axially within the moving means between the threaded rod and the moving means; and
   a helical surface in the lateral surface of the moving means which faces proximally and which substantially parallels the helical path of the indicator marking, relative to the moving means, when the moving means is rotated and the indicator marking is located axially of the helical surface;
   the indicator marking not being laterally covered by the moving means and being continuously visible proximally of, and adjacent to, the helical surface as the moving means is rotated when and only when the spacing between the anvil and the staple carrying assembly is within the range of generally suitable spacings.

2. The stapler of claim 1 wherein the indicating means (e) comprises:
   two indicator markings, located on opposite sides of the threaded rod; and
   two helical surfaces, located on opposite sides of the moving means;
   each indicator marking being continuously visible proximally of, and adjacent to, a different one of the helical surfaces as the moving means is rotated one half turn when and only when the spacing between the anvil and the staple carrying assembly is within the range of generally suitable spacings.

3. The stapler of claim 2 wherein, when the indicator markings are visible adjacent to the helical surfaces, each indicator marking extends proximally from a helical surface by a distance equal to the advance of each indicator marking during one half turn of the moving means.

4. The stapler of claim 2 wherein each helical surface comprises the distal surface of a different one of a pair of windows on opposite sides of the lateral surface of the moving means; each window having a helical shape corresponding to the helical path of an indicator marking, relative to the moving means, when the moving means is rotated and the indicator marking is located axially of the window.

5. The stapler of claim 2 wherein two sets of substantially parallel, axially extending indicia are provided on opposite sides of the lateral surface of the moving means; each set being located adjacent to, and axially of, a different one of the two helical surfaces; each indicia indicating, when an indicator marking is visible adjacent to a helical surface and is located axially of the indicia, that the anvil and the staple carrying assembly have a specific spacing between them.

6. The stapler of claim 1 wherein the indicator marking is on the lateral surface of a generally tubular, indicator sleeve which is frictionally held on the proximal end of the lateral surface of a generally cylindrical member, connected to the proximal end of the threaded rod.

7. The stapler of claim 6 wherein the indicator sleeve is on the proximal end of an indicator screw, threadedly attached to the proximal end of the threaded rod.

8. The stapler of claim 7 wherein the axial length of the threaded rod and the indicator screw, as attached, is such that, when the proximal end of the indicator screw is flush with the proximal end of the moving means, the anvil is spaced from the staple carrying assembly within the range of generally suitable spacings.

9. The stapler of claim 6 wherein the indicator marking is adjacent to the distal end of the indicator sleeve.

10. The stapler of claim 9 wherein the proximal end of the indicator marking forms an angle with the distal end of the indicator sleeve, which angle is about the same as the helix defined by the helical surface.

11. The stapler of claim 1 wherein the helical surface comprises the distal surface of a window in the lateral surface of the moving means; the window having a helical shape corresponding to the helical path of the indicator marking, relative to the moving means, when the moving means is rotated and the indicator marking is located axially of the window.

12. The stapler of claim 1 wherein a plurality of substantially parallel, axially extending indicia are provided on the lateral surface of the moving means, adjacent to, and axially of, the helical surface; each indicia indicating, when the indicator marking is visible adjacent to the helical surface and is located axially of the indicia, that the anvil and the staple carrying assembly have a specific spacing between them.

13. In a surgical stapler, provided with:
(a) a tubular housing, having an axial bore;
(b) a central rod, axially located within the bore of the housing and adapted to move distally and proximally within the bore of the housing;
(c) an anvil, mounted in a predetermined indexed orientation on the distal end of the central rod;
(d) a staple carrying assembly, mounted in a predetermined indexed orientation on the distal end of the housing, proximally of the anvil; the staple carrying assembly being adapted to be activated, so that its staples are urged distally against the anvil to fasten tissue between the anvil and the staple carrying assembly;
(e) rotatable moving means, threadedly engaged with the central rod, for moving the central rod distally and proximally within the bore of the housing upon rotation of the moving means; the moving means being rotatably connected to, and extending proximally of, the housing; and the portions of the central rod, threadedly engaged with the moving means, being positioned within the moving means; and
(f) means, connected to the central rod and the moving means, for indicating that the axial position of the distal end of the central rod relative to the distal end of the housing is such that the spacing between the anvil and the staple carrying assembly is within a range of spacings that is generally suitable for fastening tissue between the anvil and the staple carrying assembly;

the improved indicating means (f) which comprises:

two indicator markings which are on opposite sides of the lateral surface of a generally tubular indicator sleeve; the sleeve being frictionally held on the proximal end of the lateral surface of a generally cylindrical indicator screw, threadedly attached to the proximal end of the central rod; and each indicator marking being adapted to move axially within the moving means between the central rod and the moving means; and a pair of windows on opposite sides of the lateral surface of the moving means; each window having a helical distal surface which substantially parallels the helical path of an indicator marking, relative to the moving means, when the moving means is rotated and the indicator marking is located axially of the distal surface;

each indicator marking not being laterally covered by the moving means and being continuously visible proximally of, and adjacent to, a distal surface of a different one of the windows as the moving means is rotated when and only when the spacing between the anvil and the staple carrying assembly is within the range of generally suitable spacings.

* * * * *

UNITED STATES PATENT AND TRADEMARK OFFICE
CERTIFICATE OF CORRECTION

PATENT NO. : 4,379,457
DATED : April 12, 1983
INVENTOR(S) : Gravener et al.

It is certified that error appears in the above—identified patent and that said Letters Patent is hereby corrected as shown below:

| Column | Line | |
|--------|------|---|
| 1 | 22 | "very" should be --vary-- |
| 8 | 65 | "19" should be --18-- |
| 9 | 25 | "18" should be --19-- |
| 9 | 27 | "18" (first occurrence) should be --19-- |
| 10 | 47 | "38" should be --39-- |
| 11 | 46 | after "and" insert --the-- |
| 11 | 46 | "husing" should be --housing-- |
| 12 | 55 | "brough" should be --brought-- |

Signed and Sealed this

Twentieth Day of November 1984

[SEAL]

Attest:

GERALD J. MOSSINGHOFF

Attesting Officer    Commissioner of Patents and Trademarks